United States Patent
Hemmingsson et al.

(10) Patent No.: US 6,731,981 B1
(45) Date of Patent: May 4, 2004

(54) HEART STIMULATOR FOR ADMINISTERING ANTITHROMBUS THERAPY

(75) Inventors: Tryggve Hemmingsson, Sollentuna (SE); Jakub Hirschberg, Täby (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/530,384

(22) PCT Filed: Oct. 9, 1998

(86) PCT No.: PCT/SE98/01822
§ 371 (c)(1),
(2), (4) Date: Apr. 27, 2000

(87) PCT Pub. No.: WO99/21613
PCT Pub. Date: May 6, 1999

(30) Foreign Application Priority Data

Oct. 28, 1997 (SE) .................................................. 9703932

(51) Int. Cl.$^7$ ................................................ A61N 1/18
(52) U.S. Cl. ............................................. 607/13; 607/9
(58) Field of Search ................................. 607/9, 13, 5

(56) References Cited

U.S. PATENT DOCUMENTS

| | | | |
|---|---|---|---|
| 3,703,900 A | 11/1972 | Holznagel | |
| 5,002,052 A | * 3/1991 | Haluska | ........................ 607/4 |
| 5,433,729 A | 7/1995 | Adams et al. | |
| 5,464,429 A | 11/1995 | Hedberg et al. | |

FOREIGN PATENT DOCUMENTS

| CN | 1107034 | 8/1995 |
|---|---|---|
| EP | 0 727 241 | 8/1996 |

* cited by examiner

Primary Examiner—Mark Bockelman
(74) Attorney, Agent, or Firm—Schiff Harin LLP (57) ABSTRACT

A heart stimulator has a stimulation energy delivering assembly, including at least one lead adapted for implantation in contact with cardiac tissue, and an atrial arrhythmia detector, and a control unit connected to the stimulation energy delivering assembly and to the detector. The control unit controls the stimulation energy delivering assembly to deliver at least one atrial arrhythmia abolishing therapy and, if continued atrial arrhythmia is detected, to deliver antithrombus stimulation energy pulses of lower energy than a defibrillation shock, but with different timing and with sufficient energy for producing atrial contraction for increasing hemodynamic blood transportation away from the atrium and for preventing thrombi formation in the atrium. For a patient suffering from a chronic or paroxysmal noncurable atrial arrhythmia, the control unit controls the stimulation energy delivering assembly to deliver the antithrombus energy without any preceding arrhythmia abolishing therapy.

66 Claims, 11 Drawing Sheets

HEART STIMULATOR FOR ADMINISTERING ANTITHROMBUS THERAPY

BACKGROUND OF THE INVENTION

1. Field of the Invention

The present invention relates to a heart stimulator comprising stimulation energy delivering means intended to deliver stimulation energy through at least one implanted lead to the heart of a patient and an atrial arrhythmia detecting means.

2. Description of the Prior Art

There is a 2–4% prevalence of atrial fibrillation in humans around the age of 70 years. In case of chronic atrial fibrillation, paroxysmal atrial fibrillation, and other atrial arrhythmias there is a high risk of medical complications due to possible thrombi formations, such as embolism from the left side of the heart to cerebral arteries or to other arteries of the upper and lower part of the human body. In the case of thrombi formation in the right atrium or ventricle there is also a risk for accompanying embolism to the pulmonary vessels, with a risk of resulting pulmonary embolism.

Patients suffering from atrial arrythmia such as atrial fibrillation are often subject to medication with anti-thrombotic drugs, such as Dicumarol or Warfarine with the accompanying high risks of medical problems. Overdoses are associated with risks of bleeding, bruises and mental problems in relation to the elevated risk of bleeding etc., and undermedication is associated with a too low plasma concentration of Dicumarol and Warfarine with again an obvious risk of thrombi formation.

Moreover, there is a risk of low compliance to self-medication among such patients, who often are elderly. The medication also requires frequent medical check-ups of, e.g. protrombine values, to be able to adapt the level of medication to the needs of the drug metabolism in the individual patient. This means massively increasing medical care expenses. In addition thereto there are in quite a number of clinical cases contraindications to the use of drugs such as the ones mentioned above.

In spite of the frequent usage of the medical treatment described above there is no clear evidence as to the effectiveness of the treatment.

It is traditionally widely accepted that atrial thrombi form only after 2–3 days of atrial fibrillation, and that atrial thrombi in a fibrillating atrium form after the onset of the arrhythmia. Therefore, e.g. cardioversion of atrial fibrillation of less than 3 days duration without anticoagulation prophylaxis is believed to be safe and is commonly performed, see M. F. Stoddard, "Risk of Thromboembolism in New Onset or Transient Atrial Fibrillation", Progress in Cardiovascular Diseases, Vol. XXXIX, No. 1, July/August, 1996, pp. 69–80.

An implantable atrial defibrillator specially designed for keeping the energy consumption on a comparatively low level is described in U.S. Pat. No. 5,433,729, and U.S. Pat. No. 5,464,429 discloses an apparatus for defibrillation of a heart, in which sequences of stimulation pulses and defibrillation shocks are delivered to the heart. The stimulation pulses used have an amplitude and/or pulse duration which greatly exceed the amplitude and/or pulse duration of ordinary pacemaker pulses, however, the high-energy stimulation pulses contain considerably less energy than an ordinary defibrillation shock, thereby reducing the total energy consumption.

In European Application 1 0 727 241 a device for electric heart stimulation is described, which device delivers a mild therapy to achieve an electrical influence on the heart which in a gentle manner reduces the occurrence of malfunctions in the muscles of the heart for correcting or restoring a collapsed conduction system.

In the following electrical thrombosis preventive stimulation or thromboembolic prophylactic stimulation is denoted by TPS and by thromboembolic prophylactic stimulation capture or TPS capture is meant a sufficient stimulation or energy level for achieving supporting hemodynamic blood transportation away from the atrium.

SUMMARY OF THE INVENTION

An object of the present invention is to provide a heart stimulator for preventing or reducing thrombosis and embolism occurrence in case of atrial fibrillation or other atrial arrhythmia by administering an electrical therapy, this therapy not being intended for treatment of the atrial fibrillation or atrial arrhythmia in itself.

This object is achieved in accordance with the principles of the present invention in a heart stimulator which, in combination with a conventional pacing regimen, or as a stand-alone therapy, delivers pulses to cardiac tissue with an energy content lower than a conventional defibrillation shock, the energy content of the delivered pulses being sufficient to produce an atrial contraction that promotes the efficiency of hemodynamic blood transportation away from the atrium, thereby preventing thrombi formation in the atrium.

Thus, with the heart stimulator according to the invention an electrical prophylactic therapy is provided by electrical stimulation of heart tissue such that at least a partial contraction of the atrium is achieved with resulting improved hemodynamic blood transportation away from the atrium, where thrombi formation can be initialized. Thus the atrial contraction is not necessarily performed in an optimal physiological manner, but effective enough to protect the patient against thrombi formation and possible left or right sided embolic events. The heart stimulator according to the invention offers a comparatively cheap and easily performed therapy of the above discussed universally spread disease. Another advantage of the heart stimulator according to the invention is that it can be easily realized by modifying existing pacemaker and defibrillator apparatuses.

The heart stimulator according to the invention can suitably be used for providing thromboprophylactic electrical stimulation of the atrium when ordinary defibrillation therapy has not been successful within 2–3 days after the onset of the atrial arrhythmia, as discussed above. The heart stimulator according to the invention can also be used for delivering the thromboprophylactic therapy to patients having chhronic or paroxysmal, non-cureable atrial fibrillation. The therapy delivered by the heart stimulator according to the invention can also be a supplement to thromboprophylactic medication.

The antithrombus stimulation energy pulses delivered by the stimulator according to the invention are of lower energy than a defibrillation shock, but, according to an embodiment of the invention, of sufficient magnitude for causing a contraction in at least a part of atrial muscular tissue. Thus, the thromboprophylactic therapy delivered by the heart stimulator according to the invention is considerably less energy consuming than a regular defibrillation therapy.

According to another embodiment of the heart stimulator according to the invention said stimulator has a control unit which contains synchronizing circuitry which controls the energy delivery stage to deliver antithrombus stimulation energy in a phase of the cardiac cycle sufficiently separated from the vulnerable phase of the cycle. In this way the patient is protected against the triggering of dangerous cardiac events.

The heart stimulator according to the invention can be a pacemaker or a defibrillator having different modes of operation, one of these modes being a thrombo-prophylactic stimulation mode for delivery of antithrombus stimulation energy.

DESCRIPTION OF PREFERRED EMBODIMENTS

As mentioned above the heart stimulator according to the invention can easily be realized by modifying currently existing heart stimulator designs and current electrode positioning of implantable systems can be used. Contractive stimulus for thromboembolic prophylactic therapy can thus be applied directly in the right atrium, epicardially on the right and/or left atrial wall, in the coronary vein system, in and on the right ventricular wall or epicardially on the left ventricular wall. The electrode placement could be atrial appendix, atrial lateral wall, atrial septum, coronary sinus or in the upper portion of the right ventricle, preferably in the outflow tract. The thromboembolic prophylactic stimulation can be provided in the form of a contractive electrical stimulus of an energy below the defibrillation threshold value. Such low energy defibrillation or electrical convertion can be used in a crosstalk manner in the heart stimulator according to the invention. Thus a low-energy electrical ventricular stimulus of an amplitude below defibrillation therapy level can cause atrial contraction without major disturbance or side effects on the heart rhythm.

An atrial shock stimulus with or without "defibrillation capture" can be applied for thromboembolic prophylactic stimulation by the heart stimulator according to the invention. Such atrial shock stimulus can be applied directly on the right or left atrium or as interatrial crosstalk. Thromboembolic prophylactic stimuli can also be applied in the right ventricle as ventriculo-atrial crosstalk.

The heart stimulator according to the invention can also deliver thromboembolic prophylactic therapy in the form of an electric DC stimulation of heart tissue of the general kind described, however for other purposes, in the above mentioned European Application 0 727 241.

As mentioned above the heart stimulator according to the invention can be an ordinary pacemaker or defibrillator modified to deliver thromboembolic prophylactic stimulation. The heart stimulator according to the invention can, however, as well be realized as an apparatus solely for cardiac related management of thromboembolic risks and their treatment.

The thromboembolic prophylactic therapy can be applied in an automatically programmed mode or induced by a physician and/or by the patient himself or herself. The thromboembolic prophylactic therapy can be applied in varying set-ups depending on the condition of the heart conduction system of the individual patient.

Figure 1:
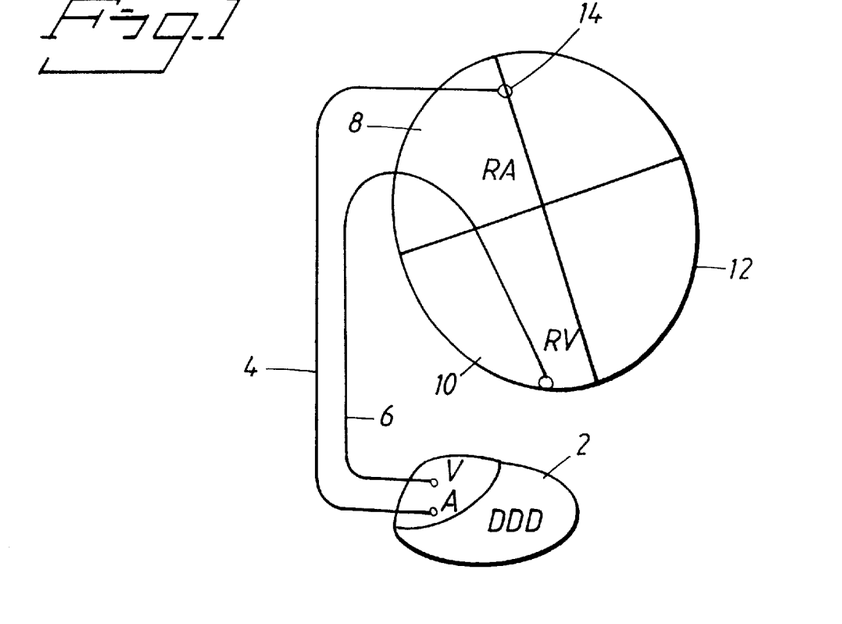
FIG. 1 schematically shows a first embodiment of the heart stimulator according to the invention in the form of a DDD-pacemaker modified to include a special antithrombus stimulation mode of operation.

The thromboembolic prophylactic stimulation can consist of a combined DC and pulsed heart tissue stimulation too. FIG. 1 shows a first embodiment of the heart stimulator according to the invention in the form of a DDD pacemaker 2 connected through leads 4, 6 to the right atrium 8 and the right ventricle 10 respectively of the heart 12 of a patient. The stimulator 2 is devised for delivering thromboembolic prophylactic stimulation pulses in the atrium and in the ventricle. In the ventricle a crosstalk stimulation is used for the thromboembolic prophylactic therapy. The atrial electrode tip 14 can be positioned in the atrial appendage, in the lateral cardiac wall or in the cardiac septal wall as shown in FIG. 1.

Figure 3:
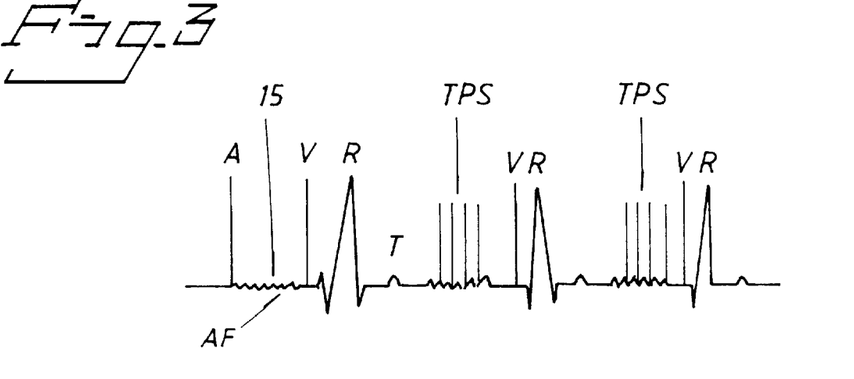
FIGS. 3–5 show corresponding diagrams for different examples of thromboprophylactic stimulation by the stimulator in FIG. 1.
Figure 4:
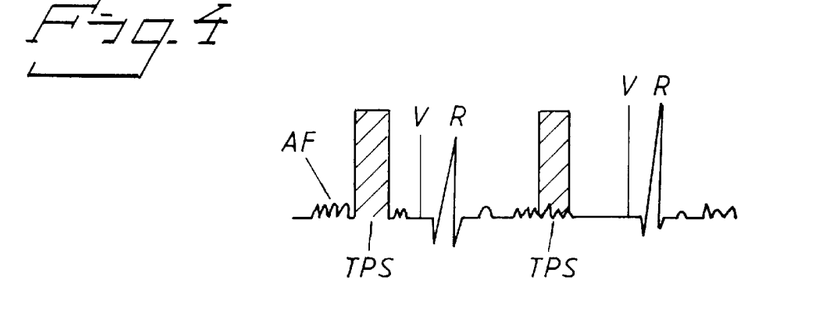

The heart stimulator 2 delivers in the thromboembolic prophylactic mode bursts of pulses or high voltage stimulation pulses in the atrium, c.f. FIGS. 3 and 4. In addition thereto pacing is performed in VVI mode or atrial pace inhibition mode with thromboembolic prophylactic crosstalk stimuli in the ventricle.

Figure 2:
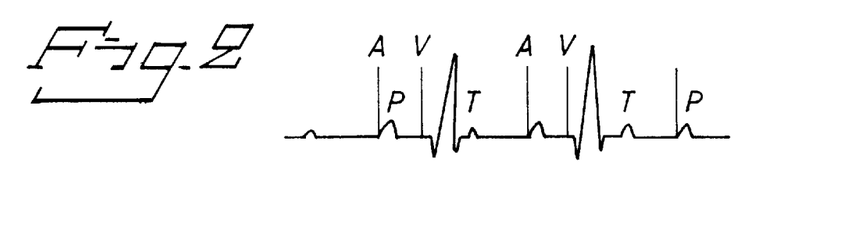
FIG. 2 is a normal DDD therapy ECG.

FIG. 2 shows the ECG for normal DDD pacing therapy disclosing an atrial pacing stimulation pulse A, the P-wave, a ventricular pacing stimulation pulse V, the QRS-complex and the T-wave.

FIG. 3 shows the ECG in a mode of operation in which the heart stimulator according to FIG. 1 delivers a burst of thromboembolic prophylactic stimulation pulses TPS followed by a ventricular stimulation pulse V. As appears from this diagram an atrial stimulation pulse A does not result in atrial capture, i.e. no P-wave is observed at 15 but a state of atrial fibrillation AF continues.

FIG. 4 shows the ECG for a mode of operation in which a strong high voltage thromboembolic prophylactic stimulation pulse TPS is delivered followed by a ventricular stimulation pacing pulse V. The thromboembolic prophylactic stimulation pulse TPS is a strong stimuli and has the character of an "extended" pacing pulse or atrial DC pulse.

The therapies illustrated in FIGS. 3 and 4 can also be combined, even in the same patient.

Figure 5:
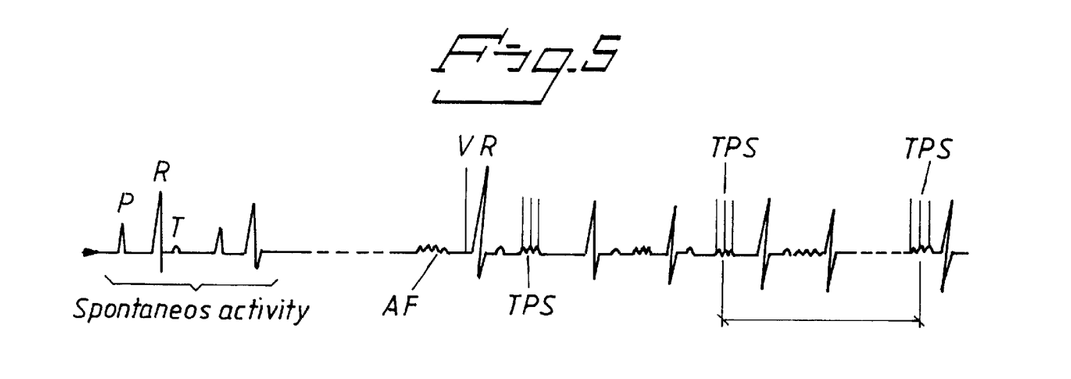

FIG. 5 shows an ECG for a mode of operation in which the application of thromboembolic prophylactic stimulation bursts TPS are separated by a plurality of RR-intervals, possibly including spontaneous heart activity with inhibited pacing and thromboembolic prophylactic treatment as indicated to the left of the figure. Bursts of thromboembolic prophylactic stimulation pulses TPS can typically be delivered a couple of times per 24 hours.

The result of the thromboembolic prophylactic therapy can be arrhythmia management or improvement as well, but this is not the main purpose, as discussed above.

Figure 6:
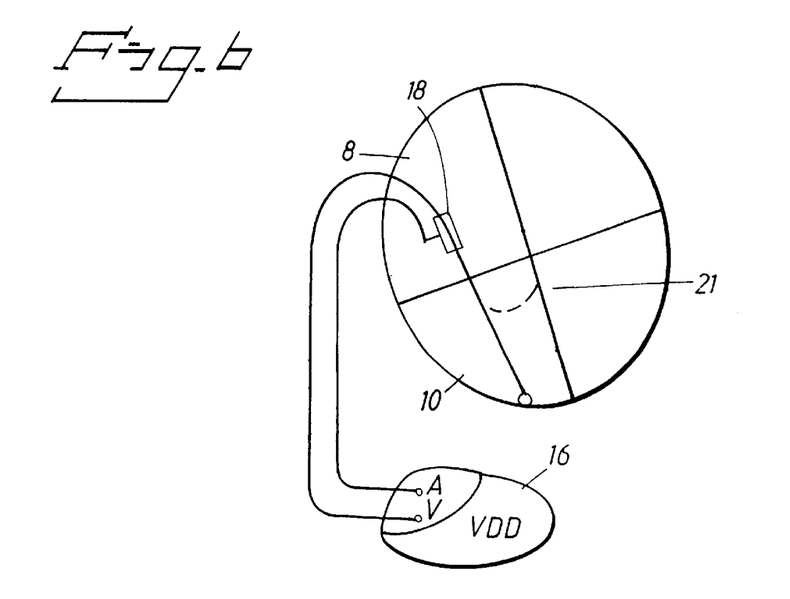
FIG. 6 shows schematically a second embodiment of the heart stimulator according to the invention in the form of a VDD pacemaker provided with an antithrombus stimulation mode of operation.

FIG. 6 shows a second embodiment of the heart stimulator according to the invention comprising a VDD pacemaker designed for atrial activity detection and thromboembolic prophylactic crosstalk stimulation in the ventricle.

Figure 7:
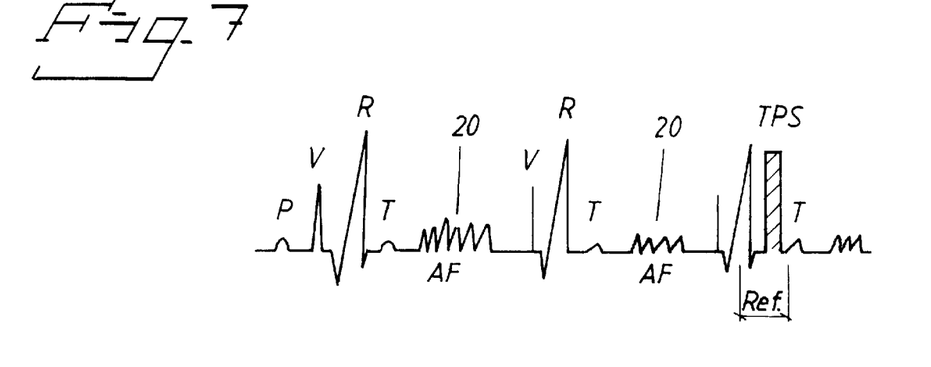
FIG. 7 shows a typical example of an ECG illustrating the operation of the embodiment shown in FIG. 6.

Thus a sensor 18 is located in the atrium 8 and 30 when an arrhythmia is sensed by this sensor 18, at 20 in FIG. 7, without the appearance of a P-wave, thromboembolic prophylactic crosstalk stimulation TPS is delivered to the ventricle in the form of a high-voltage pulse or burst of pulses during the refractory period of the ventricle Ref in FIG. 7.

For this embodiment special electrode positions, at 21 in FIG. 6, could be necessary such as the right ventricular outflow tract or close to the valvular area.

Figure 8:
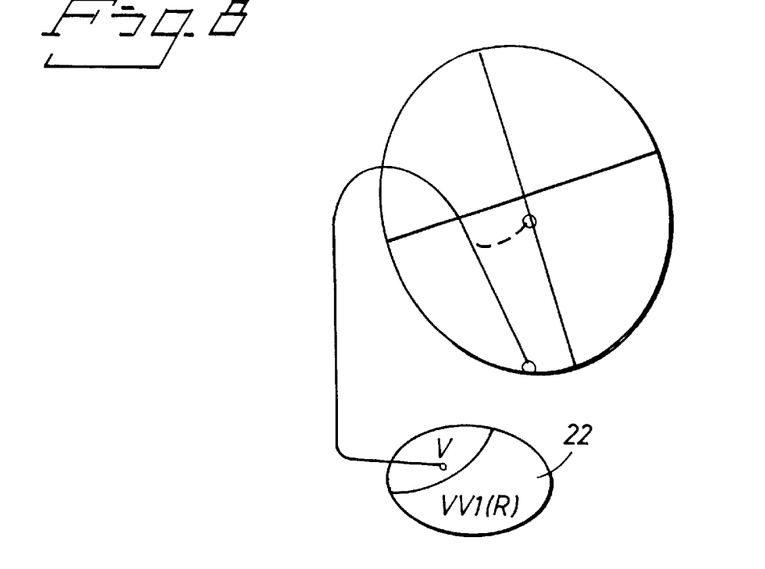
FIG. 8 shows schematically a third embodiment of the heart stimulator according to the invention in the form of a VVI pacemaker provided with an antithrombus stimulation mode of operation.

In FIG. 8 a third embodiment of the heart stimulator 22 according to the invention is shown, including a VVI pacemaker and means for atrial fibrillation detection.

Detection of atrial fibrillation can be made e.g. from R-R interval variations during the detection period. Thus atrial fibrillation can be indicated if e.g. the mean value of the RR intervals $RR_{mean}$ is much less than a $RR_{crit}$ denoting a critical value for atrial fibrillation.

Figure 9:
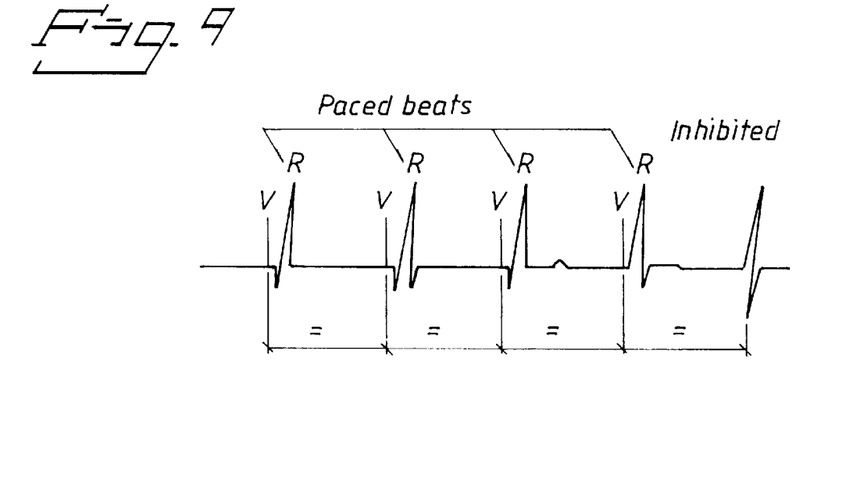
FIG. 9 shows an ECG for the heart stimulator in FIG. 8 operating in a normal pacing mode.
Figure 10:
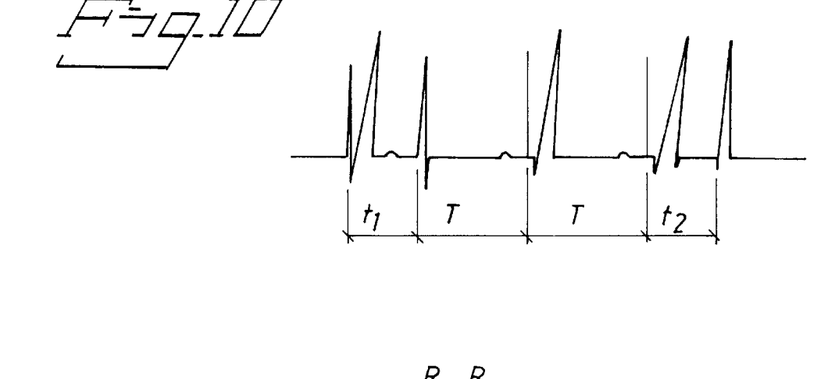
FIG. 10 shows an ECG for the heart stimulator in FIG. 8 operating in the antithrombus stimulation mode of operation.

In case of no detected atrial arrhythmia there is no need for thromboembolic prophylactic therapy and pacing in the VVI-mode is performed according to the ECG shown in FIG. 9. In case of detection of atrial fibrillation, $t1 \neq t2 \neq T$, periods of atrial fibrillation being denoted by AF in FIG. 10, thromboembolic prophylactic therapy is delivered in the form of bursts of thromboembolic prophylactic stimulation pulses in the non-vulnerable phase of the cardiac cycle, shown at 24 in the ECG in FIG. 10. In this case the thromboembolic prophylactic stimulation mode is applied according to a separate variability criteria. The thromboembolic prophylactic stimulation can also comprise delivery of high-voltage stimulation pulses. These pulses or bursts of pulses are delivered in the refractory period as mentioned above.

Figure 11:
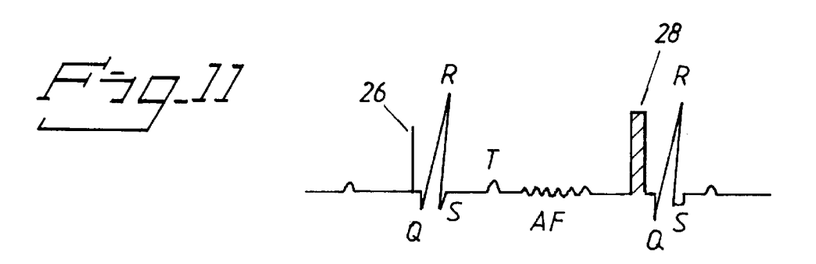
FIG. 11 is an ECG for an antithrombus stimulation mode of operation integrated with ordinary pacing stimulation.

FIG. 11 shows an ECG illustrating a situation in which the thromboembolic prophylactic stimulation, in the form of a single high-voltage pulse 28, is integrated with pacing stimulation delivered in the ventricle with a heart stimulator according to FIG. 6 or 8. The pulse 28 thus constitutes an extended, supra threshold stimulation. An ordinary pacing pulse is shown at 26.

Figure 12:
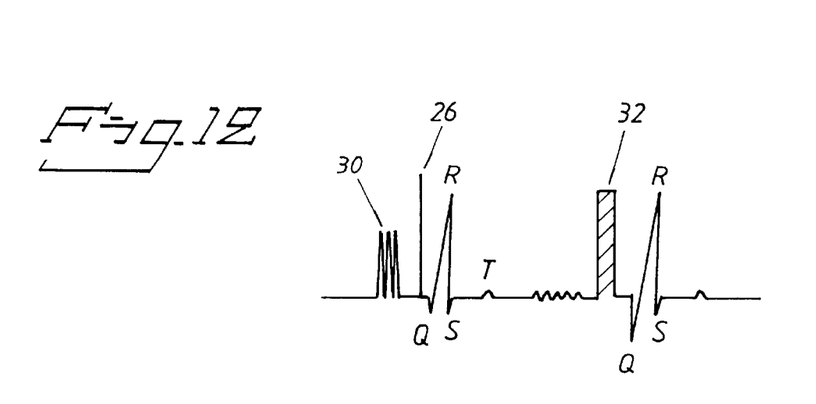
FIG. 12 shows an ECG in case of antithrombus stimulation in the form of bursts or strong crosstalk stimuli.

FIG. 12 shows the ECG in a situation with bursts of thromboembolic prophylactic stimulation pulses, at 30, the amplitude of the burst pulses being lower than the amplitude of an ordinary stimulation pulse 26, or strong thromboembolic prophylactic crosstalk stimuli 32, cf. FIG. 11.

Figure 13:
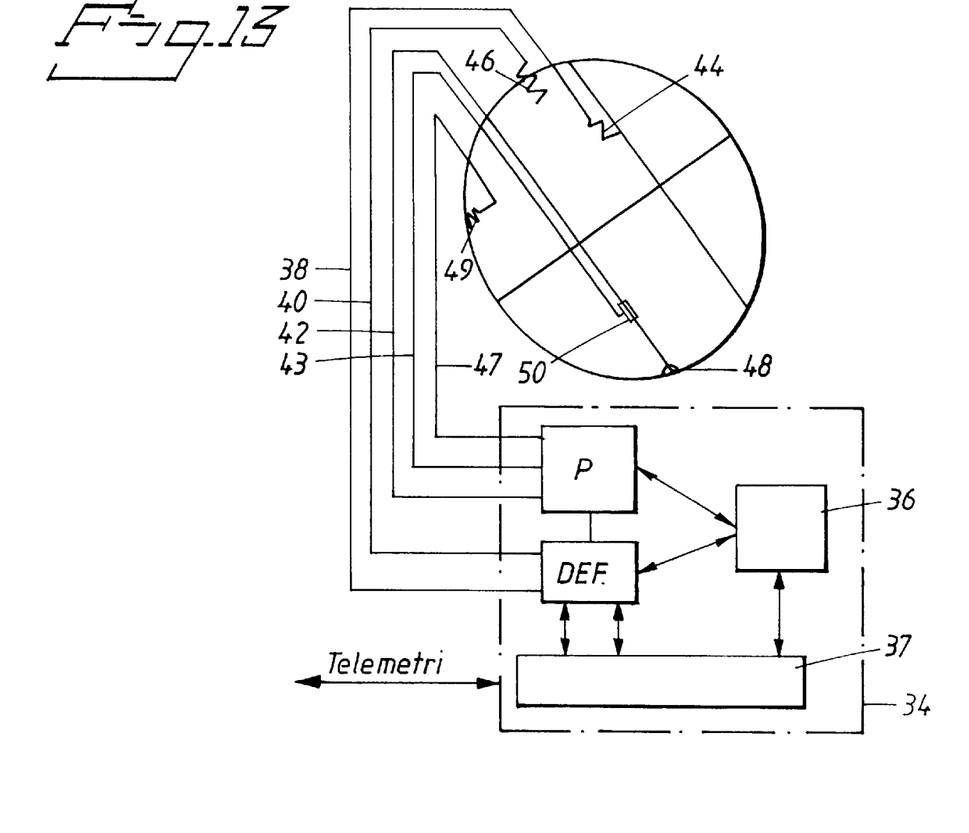
FIG. 13 shows schematically a fourth embodiment of the heart stimulator according to the invention in the form of an atrial defibrillator provided with an antithrombus stimulation mode of operation.

FIG. 13 shows a fourth embodiment of the heart stimulator according to the invention including an atrial defibrillator. This defibrillator is disposed such that, if atrial fibrillation or atrial tachycardia is detected, a shock of lower energy than an ordinary defibrillation shock is delivered periodically as thromboembolic prophylactic stimulation for improvement of blood circulation and replenishment. The thromboembolic prophylactic stimulation function is inhibited if the atrial rhythm is normalized, e.g. sinus rhythm is detected, and the thromboembolic prophylactic stimulation function is activated in case of unsuccessful atrial defibrillation therapy. The thromboembolic prophylactic stimulation therapy is controlled to be applied temporally separated from the ventricular vulnerable phase of the cardiac cycle, as mentioned above. The thromboembolic prophylactic stimulation function is synchronized to the cardiac cycle such that optimized left and right atrial blood drainage is accomplished.

The atrial defibrillator 34 thus contains a defibrillator unit DEF and a pacemaker P for stimulation in the ventricle. A control unit 36 is connected to the pacemaker P and the defibrillator DEF for controlling the delivery of thromboembolic prophylactic stimulation in response to sensed state of the heart. The defibrillator also comprises electronics 37, containing e.g. memories, programs for thromboembolic prophylactic stimulation etc. The defibrillator DEF is connected through leads 38, 40, to atrial defibrillation electrodes 44, 46 and the pacemaker P is connected through leads 42, 43, 47 to electrodes in the atrium 49 and the ventricle 48, 50 respectively. The defibrillator is communicating with an external programmer in the normal way by telemetri.

Figure 14:
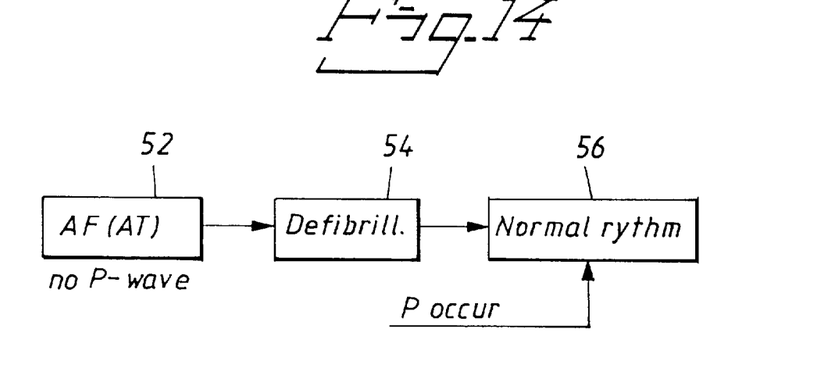
FIG. 14 is a flow diagram illustrating the ordinary operation of the heart stimulator shown in FIG. 13.

FIG. 14 shows a block diagram illustrating normal defibrillation. Thus when detecting atrial fibrillation, no P-wave, at block 52, defibrillation therapy is applied, at block 54. As a result of this therapy the heart resumes its normal atrial rhythm and P-waves appear, at block 56.

Figure 15:
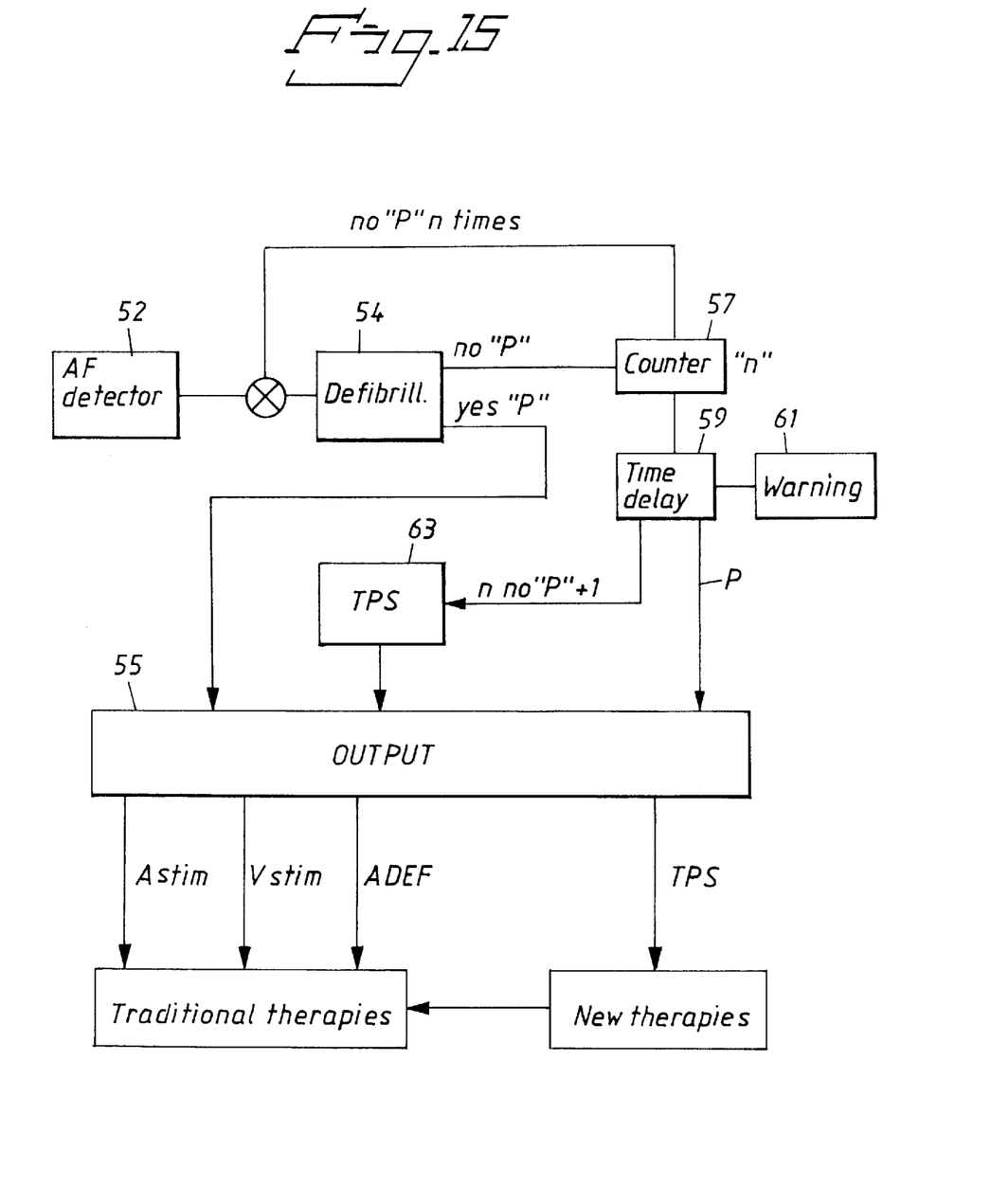
FIG. 15 is a flow diagram illustrating the antithrombus stimulation mode of operation of the heart stimulator in FIG. 13.

If atrial defibrillation is detected in block 52 in FIG. 15, a defibrillation therapy is delivered, at block 54. If a P-wave is detected as a result of the therapy atrial or ventricular Astim or Vstim is delivered in traditional therapies by the output block 55. If no P-wave is detected as a result of the defibrillation, block 54, this information is sent to a counter 57 and if "no P-wave" appears a predetermined number of times n a time delay, block 59, is started and a warning, block 61, is given. If no P-wave appears within a predetermined time delay, such that "no P-waves" appear n+1 times the output block 55 is controlled by a TPS control block 63 to deliver thromboembolic prophylactic therapy. The thromboembolic prophylactic therapy can be selectable via a program structure, in block 55, or a physician can be able to use a real time controlled "open" loop to select e.g. the number and pattern of thromboembolic prophylactic stimuli and the time between each stimulation event. This new therapy can be combined with the traditional ones.

If a P-wave appears during the mentioned predetermined time delay the output block 55 is controlled to deliver traditional therapies.

Figure 16:
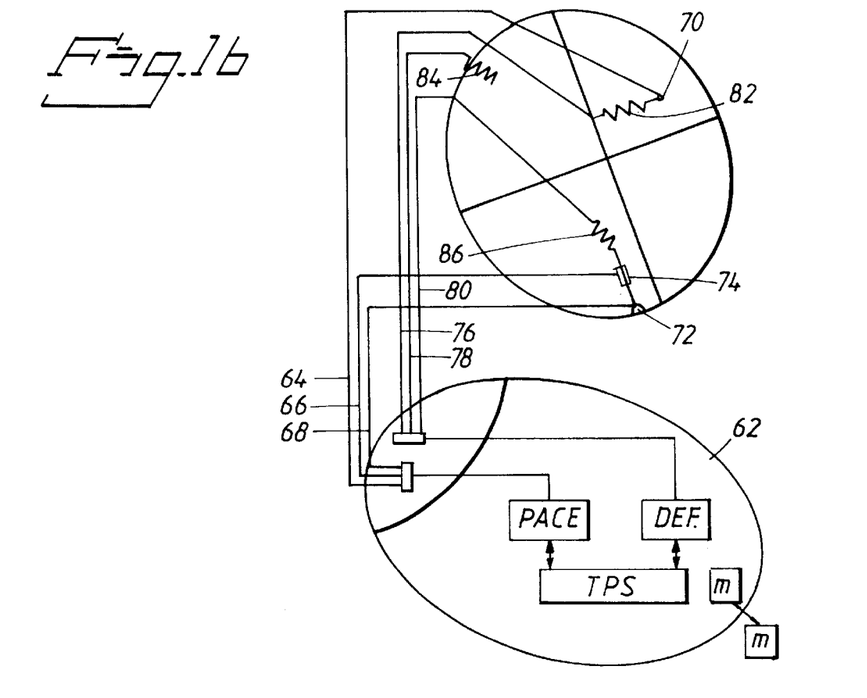
FIG. 16 shows schematically a fifth embodiment of the heart stimulator according to the invention in the form of a dual chamber defibrillator provided with a thromboembolic prophylactic stimulation circuit.

FIG. 16 shows a fifth embodiment of the heart stimulator according to the invention including a dual chamber defibrillator. Thus this heart stimulator 62 comprises a defibrillator unit DEF, a pacing unit PACE and a thromboembolic prophylactic stimulation unit TPS. The pacing unit PACE is connected via leads 64, 66, 68 to electrodes 70 for atrial pacing in coronary sinus and ventricular electrode poles 72, 74. The defibrillator unit DEF is connected through leads 76, 78, 80 to electrodes in the coronary sinus 82, in the superior vena cava 84 and in the right ventricle 86 respectively.

The heart stimulator 62 contains a memory and telemetry unit $m_1$ which communicates with an external programming unit $m_2$.

The thromboembolic prophylactic therapy can be applied on the atrium similar to anti-tachycardia therapy using pulses with voltages above the pacing stimulation pulse level. The thromboembolic prophylactic therapy can be applied simultaneously with AV-defibrillation, or together with pacing therapy of the patient by mode switching between the different modes of operation of the heart stimulator 62.

Figure 17:
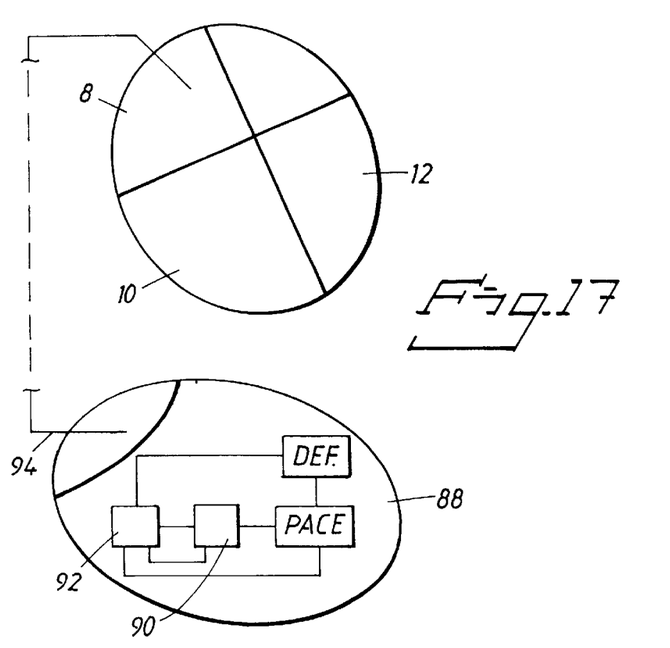
FIG. 17 shows schematically a sixth embodiment of the heart stimulator according to the invention including a device for delivering DC thromboembolic prophylactic current injection.

In FIG. 17 a sixth embodiment of the heart stimulator according to the invention is shown. The stimulator 88 comprises a defibrillator unit DEF, a pacing unit PACE, a DC-voltage source 90 connected to a unit 92 for delivering thromboembolic prophylactic therapy. The stimulator 88 is connected through a lead 94 to the atrium 8 of the heart 12 for delivering thromboembolic prophylactic DC current injection therapy to the right atrium 8.

The electrode system can be similar to the electrode system of a pacing device or an atrial defibrillator system.

Figure 18:
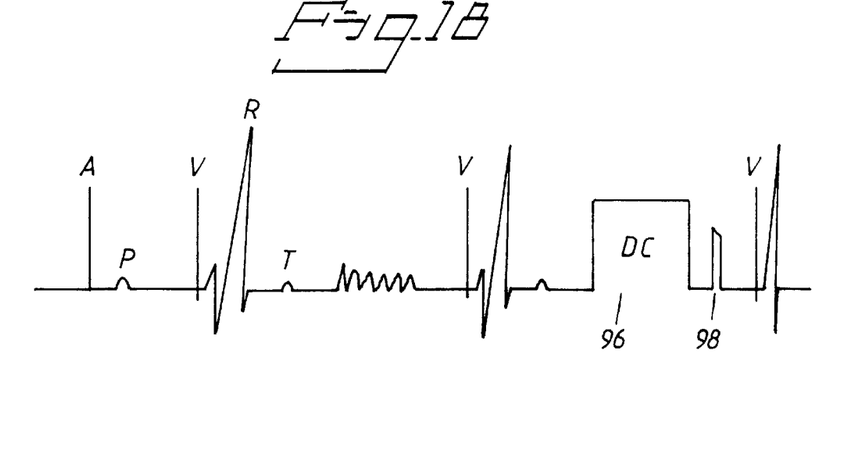
FIG. 18 shows an ECG recorded during operation of the heart stimulator in FIG. 17.

The treatment of the heart tissue with DC as a thromboembolic prophylactic therapy can be performed with different characteristics. FIG. 18 shows an ECG with one example of DC energy delivery during a comparatively long time, at 96, and during a shorter time, at 98.

The term DC energy or DC therapy means that kind of mild therapy defined in the previously mentioned European Application 0 727 241.

The stimulator in FIG. 17 can also be of an atrio-ventricular setup with electrodes for the thromboembolic prophylactic therapy similar to the electrodes of a dual chamber defibrillator system, and the pacing unit PACE can be adapted for stimulation both in the atrium and the ventricle. The ECG in FIG. 18 shows the delivery of both atrial pacing pulses A and ventricular pacing pulses V.

The DC energy and other types of TPS therapies can be delivered between two selectable electrodes which can be implantable transvascular or extravascular electrodes, including epicardial electrodes.

Figure 19:
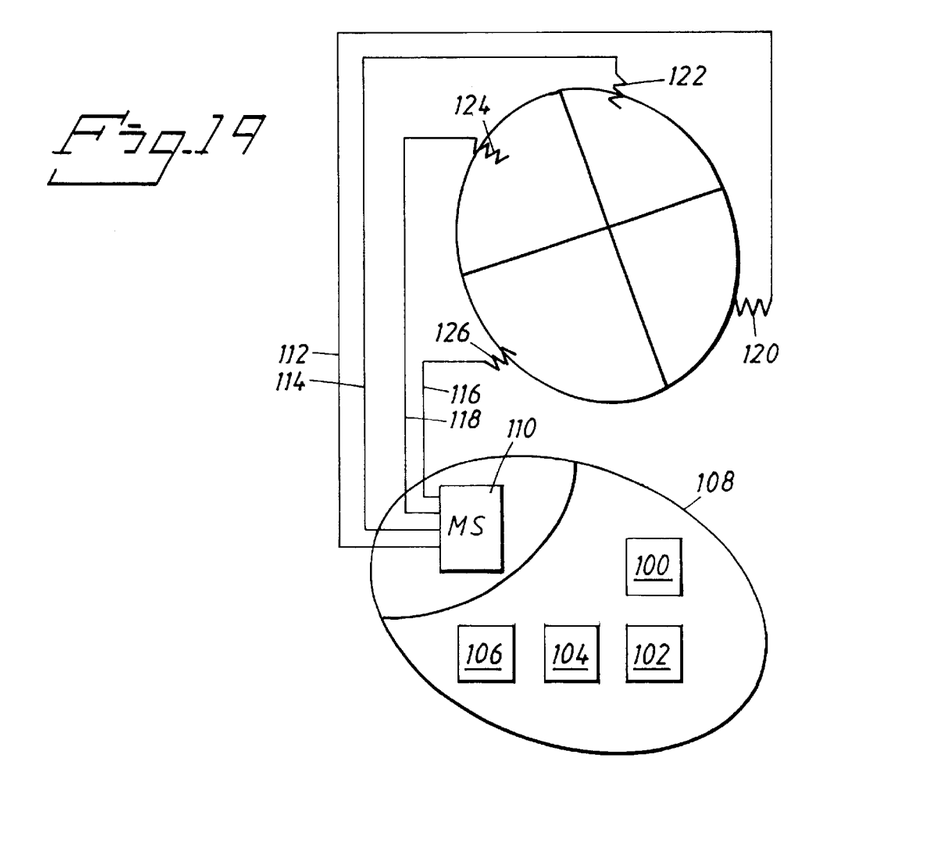
FIG. 19 shows schematically a seventh embodimenet of the heart stimulator according to the invention including a multisite thromboembolic prophylactic stimulation device.
Figure 20:
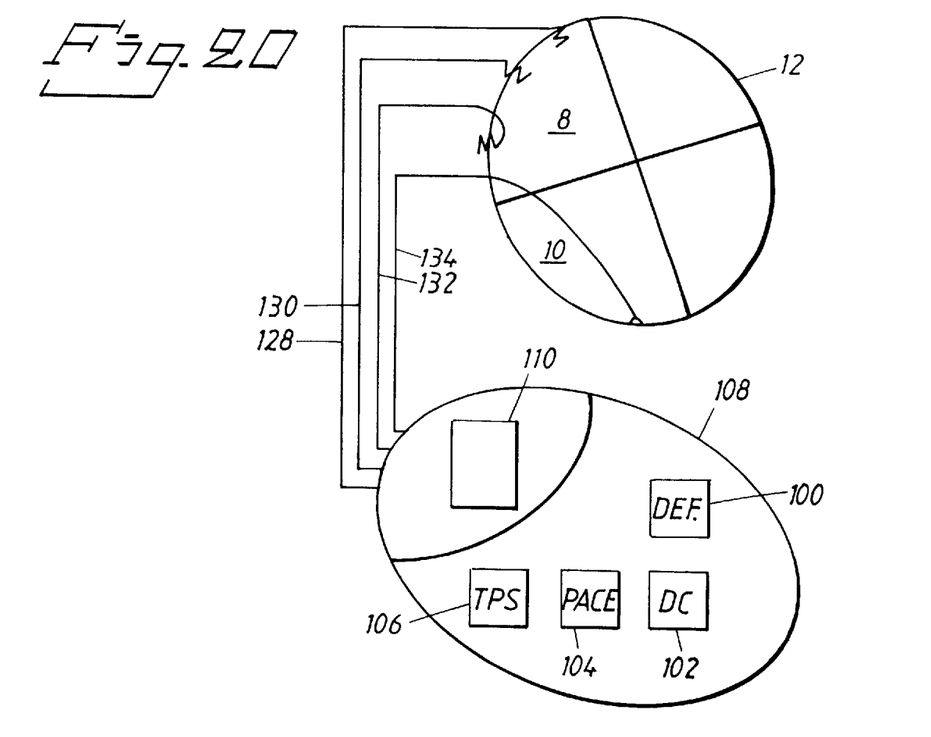
FIG. 20 shows schematically an eighth embodiment of the heart stimulator according to the invention provided with a multisite and/or multichamber thromboembolic prophylactic stimulation device.

FIGS. 19 and 20 show two more modifications of the stimulator shown in FIG. 17 for multi-site and/or multi-chamber thromboembolic prophylactic stimulation. These embodiments of the heart stimulator according to the invention comprise a defibrillator unit 100, a pacing unit 102, a DC voltage unit 104 and a thromboembolic prophylactic stimulation unit 106 as in the embodiment shown in FIG. 17. The stimulator further comprises a multisite unit 110 for connecting the stimulator 108 to a plurality of electrode leads 112, 114, 116, 118. In the embodiment shown in FIG. 19 the stimulator 108 is connected to the heart 12 through four electrode leads 112, 114, 116, 118 with epicardial electrodes 120, 122, 124, and 126 respectively. Thus with this embodiment multisite thromboembolic prophylactic stimulation can be provided.

FIG. 20 shows an alternative embodiment for providing multi-site unichamber thromboembolic prophylactic stimulation. Thus thromboembolic prophylactic stimulation of the atrium 8 can be applied through the leads 128, 130, 132,. In addition thereto the stimulator 108 is connected to the ventricle 10 through a lead 134 for ventricular stimulation (and possibly sensing).

The shown multi-site atrial electrode array can be realized as one multi-polar atrial electrode.

In these embodiments different kinds of therapy (pacing, defibrillation, thromboembolic prophylactic therapy) can be performed simultaneously or sequentially.

The described embodiments of the heart stimulator according to the invention can deliver thromboembolic prophylactic therapy of different kinds. Thus the thromboembolic prophylactic stimulation can comprise ordinary "standard" pacing pulses with amplitudes and/or energies below pacing threshold values, equal to the pacing threshold value or above this threshold value. The thromboembolic prophylactic stimulation can consist in burst therapy similar to the therapy delivered by known antitachy pacing systems. The thromboembolic prophylactic stimulation can comprise pacing with DC voltage and/or "defibrillator therapy". The defibrillation therapy is then performed with energy levels below those of ordinary defibrillation, but mostly above pacing stimulation energy levels in atrium and ventricle. The thromboembolic prophylactic stimulation capture is obtained when the stimulation or energy level is sufficient for achieving or supporting haemodynamic blood transportation away from the atrium. Relevant TPS capture is verified by the physician during implantation or follow-up procedures. Such evaluation can be made on the basis of e.g. fluoroscopy, echocardiography, ultrasound Doppler measurements, and atrial related ECG pattern changes.

Figure 21:
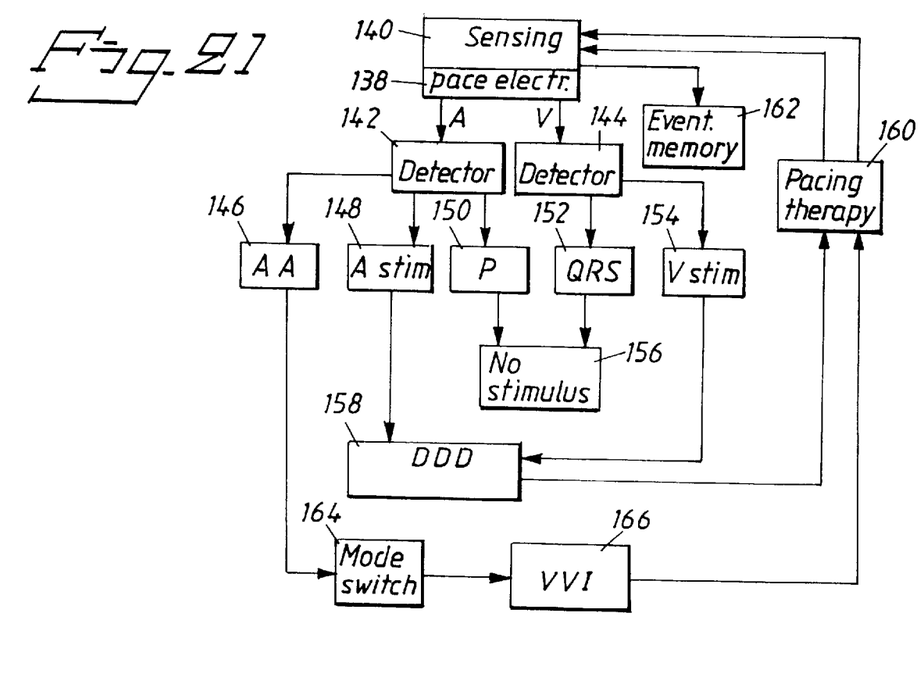
FIG. 21 is a block diagram illustrating the operation of a conventional pacing system provided with a mode switch.

FIG. 21 shows a block diagram of a conventional pacing system with mode switch comprising pacing electronics 138 and a sensing unit 140. By atrial and ventricular detectors 142 and 144 respectively the status of the atrium—atrial arrhythmia 146, atrial stimulation 148 and sensed P-wave 150—and of the ventricle—QRS complex 152 or ventricular stimulation 154—are detected.

In case of P-wave detection, block 150, and QRS complex detection, block 152, no stimulation is given to the heart, block 156. In case of atrial and ventricular stimulation the pacing system is operating in a DDD mode, block 158, and its operation is fed back through the block pacing therapy 160 to the sensing unit 140.

An event memory 162 is also connected to the sensing unit 140 for storing sensed cardiac events.

In case of detection of atrial arrhythmia the mode of operation is switched to a VVI mode, blocks 164, 166.

Figure 22:
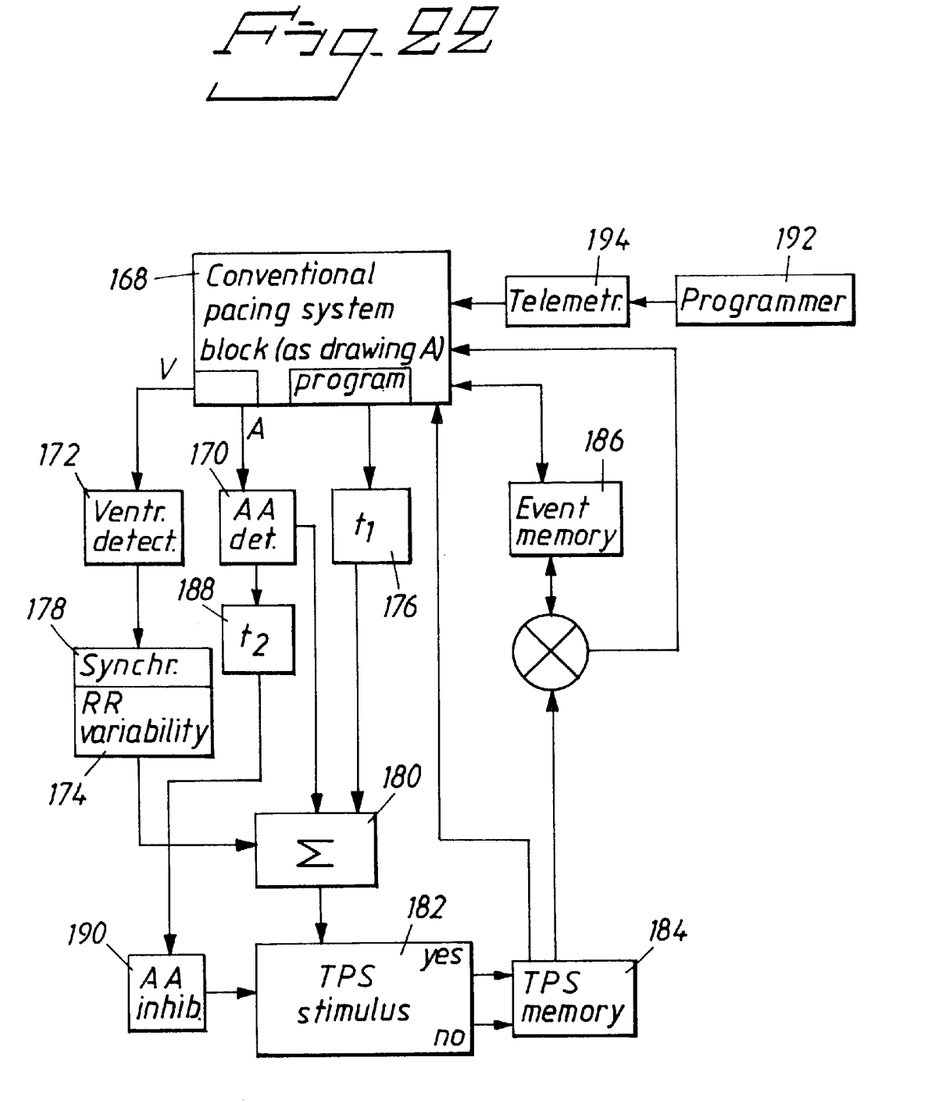
FIG. 22 is a block diagram illustrating the operation of a heart stimulator according to the invention including a conventional pacing system with TPS electronics.

FIG. 22 shows a heart stimulator according to the invention including a pacing system of the type shown in FIG. 21 and provided with means for thromboembolic prophylactic therapy. Thus block 168 represents the pacing system in FIG. 21. Atrial arrhythmias are detected by an atrial detector 170. Atrial arrhythmias can, however, also be jointly detected in the ventricle from R-R interval variations, blocks 172, 174. $t_1$ denotes a time constant for therapy interval programming, block 176. This time constant $t_1$ can vary from once every second R-R interval to twice daily.

The information from block 170 about possible detected atrial arrhythmias together with information from block 174 about the detected R R variability and synchronizing information from block 178 and the time constant $t_1$, block 176, are supplied to the summing unit 180, which in response to these information controls the thromboembolic prophylactic stimulation means 182. The resulting operation of the thromboembolic prophylactic stimulation means 182 is stored in a memory 184 and this information is fed back to the pacing system 168. The memory 184 is also connected to the cardiac event memory 186 which in its turn is connected to the pacing system 168, too.

The designation $t_2$, block 188, denotes a time constant for switching from active thromboembolic prophylactic therapy mode into a supervising mode in case of detected atrial arrhythmia inhibition, block 190.

An external programmer 192 is by telemetric means 194 communicating with the pacing system 168 in a conventional manner. Programmable parameters are magnitudes of the time constants $t_1$ and $t_2$, pulse morphology, pulse shape (slew rate, decay time), pulse width, pulse amplitude, pulse sequence, pulse burst or no pulse burst, pulse burst morphology and different therapeutic intervals.

Figure 23:
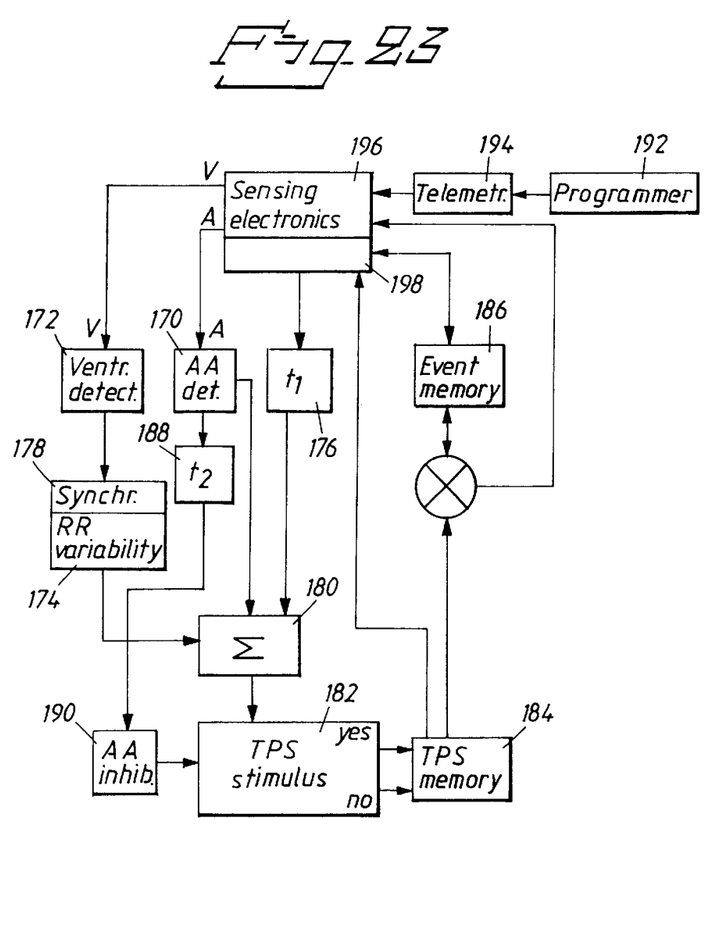
FIG. 23 is a block diagram illustrating the operation of a heart stimulator according to the invention without a pacing system.

Patients previously not equipped with a pacemaker system or a defibrillator will receive a heart stimulator according to the invention just including a special thromboembolic prophylactic stimulation device as illustrated in FIG. 23. This embodiment is similar to the embodiment shown in FIG. 22 with the exception that there is no pacing system 168. For controlling the operation of this heart stimulator sensing electronics 196 and controlling electronics 198 are provided for controlling the operation in response to received information. For the rest the same reference numerals are used as in FIG. 22.

Figure 24:
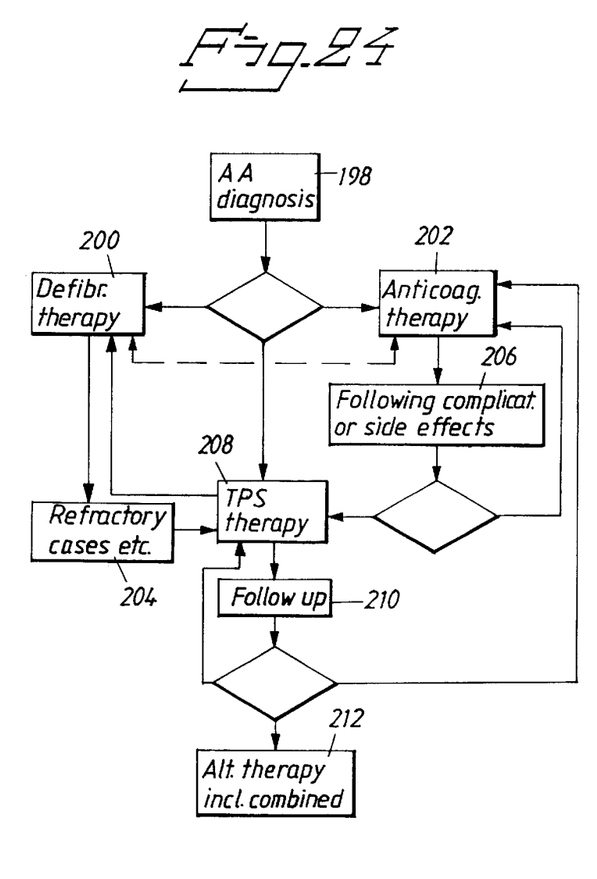
FIG. 24 is a flow chart exemplifying the therapy decision making in connection with a heart stimulator of the type shown in FIG. 23.

FIG. 24 is a flow chart illustrating the therapy decision making according to the invention for an atrial arrhythmia patient.

In case of atrial arrhythmia diagnosis 198 defibrillating therapy 200 and/or an anti-blood coagulation therapy 202 are applied. If the patient is not positively responding to the defibrillating therapy, block 204, and/or if there are complications or undesirable side effects from the anti-coagulation therapy, thromboembolic prophylactic stimulation therapy delivered by the heart stimulator according to the invention is applied after suitable time delays, block 208. The result of this therapy is followed up, block 210, and fed back to the thromboembolic prophylactic stimulation means, block 208, for possibly modifying the therapy. Depending on the results of the thromboembolic prophylactic therapy also alternatives, including combinations of different therapies, can be considered, block 212.

Thus by using e.g. a pacemaker lead of conventional uni- or bipolar type, placed in the right atrium of the heart or epicardially at the left atrium it is possible with a heart stimulator according to the invention to stimulate the left atrium to contract periodically in order to prevent thrombous formation in an atrium of regular size or in a dilated atrium. With the heart stimulator according to the invention the need for anticoagulent or related antithrombotic medication is reduced. It also reduces the need for electroconvertion with its risks, costs and ineffectiveness.

The therapy applied by the heart stimulator according to the invention is a more "powerful stimulation" than ordinary pacing stimulation in order to achieve an intermittent antithrombotic contractive therapy.

The decision for implementing the thromboembolic prophylactic therapy by the heart stimulator according to the invention is in the individual case to be taken by the physician. The therapy can be implemented by an automatic adaptive algorithm or by a custom defined therapy program with selectable semi-automatic limitations (stimulation period during day or night, number and morphology of consecutive pulses during the stimulation period, etc.), safeguarding escape mode in case of ventricular arrhythmia detection, and by program selectable time limiting supervising mode at detection of recurrent normal atrial sinus rhythm, e.g. in paroxysmal atrial fibrillation. Usually the thromboembolic prophylactic therapy is applied after about a 24 hour period of atrial arrhythmia, e.g. atrial fibrillation.

The heart stimulator according to the invention comprises at least one thromboembolic prophylactic stimulation electrode and possibly at least one sensing electrode. The sensing electrode is not necessarily implanted in the heart and/or on the heart, however, it is to be positioned for best P-wave and QRS detection and monitoring, which also includes multisite setup electrode applications as described above.

The risk of thrombous formation can be determined by pressure, flow and Doppler measurements. By forming an average value of the ECG signal, especially in relation to the P-wave, during a plurality of cardiac cycles before the thromboembolic prophylactic therapy, and after this therapy the difference between these average values gives an indication of the effect of the therapy. Sometimes the trembling motion of a fibrillating atrium seem to promote thrombous formation.

Although modifications and changes may be suggested by those skilled in the art, it is the invention of the inventors to embody within the patent warranted heron all changes and modifications as reasonably and properly come within the scope of their contribution to the art.

We claim as our invention:

1. A heart stimulator comprising: a stimulation energy delivering assembly including at least one lead, adapted for implantation in contact with cardiac tissue, for delivering stimulation energy via said lead, an atrial arrhythmia detector, and a control unit connected to said detector and to said stimulation energy delivering assembly for controlling said stimulation energy delivering assembly to deliver at least one primary atrial arrhythmia abolishing stimulus via said lead and after a predetermined time, if continued atrial arrhythmia is detected by said detector, antithrombus stimulation energy in a form selected from the group consisting of pulses and burst of pulses of different timing and energy levels from the primary stimulus for producing an atrial contraction that promotes hemodynamic blood transportation away from the atrium and prevents thrombi formation in the atrium.

2. The heart stimulator according to claim 1 wherein said control unit includes a time delay stage for delaying delivery of said antithrombus stimulation energy for a predetermined time delay after one of a detected onset of atrial arrhythmia by said detector and after a terminated unsuccessful abolishing of atrial arrhythmia by said primary stimulus.

3. The heart stimulator according to claim 2, wherein said time delay is programmable.

4. The heart stimulator according to claim 2, wherein said predetermined time delay is at least 24 hours.

5. The heart stimulator according to claim 1, wherein said control unit is manually actuatable for manual determination of a time of delivery of said antithrombus stimulation energy.

6. The heart stimulator according to claim 1 wherein said atrial arrhythmia detector is a P-wave detector.

7. The heart stimulator according to claims 1 wherein said atrial arrhythmia detector detects atrial arrhythmia from sensed R-R interval variations.

8. The heart stimulator according to claim 1 wherein said antithrombus stimulation energy is sufficient for causing a contraction in at least a part of atrial muscular tissue.

9. The heart stimulator according to claim 1 comprising a programming unit for programming a morphology of said pulses or bursts of pulses.

10. The heart stimulator according to claim 9, wherein said programming unit programs a time interval between consecutive antithrombus stimulation pulses or consecutive bursts of antithrombus stimulation pulses.

11. The heart stimulator according to claim 1 wherein said control unit controls said energy delivering assembly to said deliver antithrombus stimulation energy as a continuous pulse of DC current.

12. The heart stimulator according to claim 1 wherein said control unit controls said stimulation energy delivering assembly to periodically deliver said antithrombus stimulation energy.

13. The heart stimulator according to claim 12, wherein said control unit controls said energy delivering assembly to deliver said antithrombus stimulation energy at a frequency between twice a day and every other heartbeat.

14. The heart stimulator according to claim 1 wherein said control unit includes synchronizing means for synchronizing delivery of said antithrombus stimulation energy with a cardiac cycle, detected by sad detector, to optimize atrial drainage.

15. The heart stimulator according circuitry controls to claim 14, wherein said synchronizing circuitry controls said stimulation energy delivery assembly to deliver said antithrombus stimulation energy in a phase of the cardiac cycle separated from a vulnerable phase of the ventricle.

16. The heart stimulator according to claim 14, wherein said synchronizing circuit controls said stimulation energy delivery assembly to deliver said pulses or bursts of pulses respectively separated by a plurality of cardiac cycles.

17. The heart stimulator according to claim 14 said synchronizing circuit controls said stimulation energy delivery assembly to deliver said pulses or bursts of pulses before a QRS complex in the cardiac cycle.

18. The heart stimulator according to claim 1 wherein said stimulation energy delivery assembly includes two electrodes selected from the group consisting of transvascular electrodes and extravascular electrodes.

19. The heart stimulator according to claim 1 wherein said lead is adapted for implantation into the atrium and is selected from the group consisting of leads and bipolar leads.

20. The heart stimulator according to claim 1 wherein said lead is adapted for implantation into the coronary vein system including coronary sinus ostium area.

21. The heart stimulator according to claim 1 wherein said lead is selected from the group consisting of leads adapted for implantation in the right ventricle and leads adapted for implantation on the right ventricular wall.

22. The heart stimulator according to claim 21, wherein said lead is a lead implantable in the right ventricle, and wherein said stimulation energy delivery assembly delivers antithrombus stimulation pulses or bursts of antithrombus stimulation pulses as ventriculo-atrial crosstalk.

23. The heart stimulator according to claim 22, wherein said control unit controls said stimulation energy delivering assembly to deliver said crosstalk antithrombus stimulation pulses or said crosstalk bursts of antithrombus stimulation pulses in a time interval between a QRS-complex and a T-wave.

24. The heart stimulator according to claim 1 wherein said lead is an atrial multipolar electrode lead for multisite antithrombus therapy of the atrium.

25. The heart stimulator according to claims 1 wherein said stimulation energy delivering assembly includes a plurality of electrode leads for multisite epicardial antithrombus therapy.

26. The heart stimulator according to claim 25, wherein said plurality of leads is adapted for unichamber antithrombus therapy.

27. The heart stimulator according to claim 25, wherein said plurality of leads is adapted for multichamber antithrombus therapy.

28. The heart stimulator according to claim 25, wherein said plurality of electrode leads comprises epicardial electrodes for respective implantation at sites selected from the group consisting of on the right left atrial wall, the right ventricular wall and the left ventricular wall.

29. The heart stimulator according to claim 1 wherein said lead is a lead implantable in the left atrium, and wherein said stimulation energy delivering assembly delivers antithrombus stimulation pulses or bursts of antithrombus stimulation pulses as inter-atrial crosstalk.

30. The heart stimulator according to claim 1 wherein said stimulation energy delivering assembly is adapted for delivery, via said lead, of antithrombus stimulation energy in the right ventricle outflow tract or in the vicinity of the valvular area.

31. The heart stimulator according to claim 1 wherein said control unit controls said stimulation energy delivering assembly to deliver said antithrombus stimulation energy in an antithrombus mode, and wherein said control unit also controls said stimulation energy delivering assembly, in a pacing mode, to deliver pacing pulses to cardiac tissue via said lead.

32. The heart stimulator according to claim 1 wherein said control unit controls said stimulation energy delivering assembly to deliver said antithrombus stimulation energy in an antithrombus mode, and wherein said control unit also controls said stimulation energy delivering assembly, in a defibrillation mode, to deliver defibrillation pulses to cardiac tissue via said lead.

33. The heart stimulator according to claim 1 wherein said control unit controls said antithrombus stimulation energy assembly to deliver said antithrombus stimulation energy as a single continuous DC pulse combined with antiarrhythmic therapy.

34. A heart stimulator comprising: a stimulation energy delivering assembly including at least one lead, adapted for implantation in contact with cardiac tissue, for delivering stimulation energy via said lead, an atrial arrhythmia detector, and a control unit connected to said detector and to said stimulation energy delivering assembly for controlling said stimulation energy delivering assembly to deliver antithrombus stimulation energy in a form selected from the group consisting of pulses and burst of pulses of lower energy than a defibrillation shock for producing atrial contraction for increasing hemodynamic blood transportation away from the atrium and preventing thrombi formation in the atrium.

35. The heart stimulator according to claim 34 wherein said control unit includes a time delay stage for delaying delivery of said antithrombus stimulation energy for a predetermined time delay after one of a detected onset of atrial arrhythmia by said detector and after a terminated unsuccessful abolishing of atrial arrhythmia by said primary stimulus.

36. The heart stimulator according to claim 35, wherein said time delay is programmable.

37. The heart stimulator according to claim 35, wherein said predetermined time delay is at least 24 hours.

38. The heart stimulator according to claim 34, wherein said control unit is manually actuatable for manual determination of a time of delivery of said antithrombus stimulation energy.

39. The heart stimulator according to claim 34 wherein said atrial arrhythmia detector is a P-wave detector.

40. The heart stimulator according to claims 34 wherein said atrial arrhythmia detector detects atrial arrhythmia from sensed R-R interval variations.

41. The heart stimulator according to claim 34 wherein said antithrombus stimulation energy is sufficient for causing a contraction in at least a part of atrial muscular tissue.

42. The heart stimulator according to claim 34 comprising a programming unit for programming a morphology of said pulses or bursts of pulses.

43. The heart stimulator according to claim 42, wherein said programming unit programs a time interval between consecutive antithrombus stimulation pulses or consecutive bursts of antithrombus stimulation pulses.

44. The heart stimulator according to claim 34 wherein said control unit controls said energy delivering assembly to said deliver antithrombus stimulation energy as a continuous pulse of DC current.

45. The heart stimulator according to claim 34 wherein said control unit controls said stimulation energy delivering assembly to periodically deliver said antithrombus stimulation energy.

46. The heart stimulator according to claim 45, wherein said control unit controls said energy delivering assembly to deliver said antithrombus stimulation energy at a frequency between twice a day and every other heartbeat.

47. The heart stimulator according to claim 34 wherein said control unit includes synchronizing means for synchronizing delivery of said antithrombus stimulation energy with a cardiac cycle, detected by sad detector, to optimize atrial drainage.

48. The heart stimulator according circuitry controls to claim 47, wherein said synchronizing circuitry controls said stimulation energy delivery assembly to deliver said antithrombus stimulation energy in a phase of the cardiac cycle separated from a vulnerable phase of the ventricle.

49. The heart stimulator according to claim 47, wherein said synchronizing circuit controls said stimulation energy delivery assembly to deliver said pulses or bursts of pulses respectively separated by a plurality of cardiac cycles.

50. The heart stimulator according to claim 47 said synchronizing circuit controls said stimulation energy delivery assembly to deliver said pulses or bursts of pulses before a QRS complex in the cardiac cycle.

51. The heart stimulator according to claim 34 wherein said stimulation energy delivery assembly includes two electrodes selected from the group consisting of transvascular electrodes and extravascular electrodes.

52. The heart stimulator according to claim 34 wherein said lead is adapted for implantation into the atrium and is selected from the group consisting of leads and bipolar leads.

53. The heart stimulator according to claim 34 wherein said lead is adapted for implantation into the coronary vein system including coronary sinus ostium area.

54. The heart stimulator according to claim 34 wherein said lead is selected from the group consisting of leads adapted for implantation in the right ventricle and leads adapted for implantation on the right ventricular wall.

55. The heart stimulator according to claim 54, wherein said lead is a lead implantable in the right ventricle, and wherein said stimulation energy delivery assembly delivers antithrombus stimulation pulses or bursts of antithrombus stimulation pulses as ventriculo-atrial crosstalk.

56. The heart stimulator according to claim 55, wherein said control unit controls said stimulation energy delivering assembly to deliver said crosstalk antithrombus stimulation pulses or said crosstalk bursts of antithrombus stimulation pulses in a time interval between a QRS-complex and a T-wave.

57. The heart stimulator according to claim 34 wherein said lead is an atrial multipolar electrode lead for multisite antithrombus therapy of the atrium.

58. The heart stimulator according to claims 34 wherein said stimulation energy delivering assembly includes a plurality of electrode leads for multisite epicardial antithrombus therapy.

59. The heart stimulator according to claim 58, wherein said plurality of leads is adapted for unichamber antithrombus therapy.

60. The heart stimulator according to claim 58, wherein said plurality of leads is adapted for multichamber antithrombus therapy.

61. The heart stimulator according to claim 58, wherein said plurality of electrode leads comprises epicardial electrodes for respective implantation at sites selected from the group consisting of on the right left atrial wall, the right ventricular wall and the left ventricular wall.

62. The heart stimulator according to claim 34 wherein said lead is a lead implantable in the left atrium, and wherein said stimulation energy delivering assembly delivers antithrombus stimulation pulses or bursts of antithrombus stimulation pulses as inter-atrial crosstalk.

63. The heart stimulator according to claim 34 wherein said stimulation energy delivering assembly is adapted for delivery, via said lead, of antithrombus stimulation energy in the right ventricle outflow tract or in the vicinity of the valvular area.

64. The heart stimulator according to claim 34 wherein said control unit controls said stimulation energy delivering assembly to deliver said antithrombus stimulation energy in an antithrombus mode, and wherein said control unit also controls said stimulation energy delivering assembly, in a pacing mode, to deliver pacing pulses to cardiac tissue via said lead.

65. The heart stimulator according to claim 34 wherein said control unit controls said stimulation energy delivering assembly to deliver said antithrombus stimulation energy in an antithrombus mode, and wherein said control unit also controls said stimulation energy delivering assembly, in a defibrillation mode, to deliver defibrillation pulses to cardiac tissue via said lead.

66. The heart stimulator according to claim 34 wherein said control unit controls said antithrombus stimulation energy assembly to deliver said antithrombus stimulation energy as a single continuous DC pulse combined with antiarrhythmic therapy.

* * * * *